(12) United States Patent
Brakel et al.

(10) Patent No.: US 7,495,088 B1
(45) Date of Patent: Feb. 24, 2009

(54) MODIFIED NUCLEOTIDE COMPOUNDS

(75) Inventors: Christine L. Brakel, Brightwaters, NY (US); James G. Wetmur, Scarsdale, NY (US); Robin S. Quartin, Bedminster, NJ (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 0 days.

(21) Appl. No.: 08/479,999

(22) Filed: Jun. 28, 1994

Related U.S. Application Data

(63) Continuation of application No. 07/446,235, filed on Dec. 4, 1989, now abandoned.

(51) Int. Cl.
*C12Q 1/68* (2006.01)
*C12P 21/06* (2006.01)
*C07H 21/02* (2006.01)
*C07H 21/04* (2006.01)

(52) U.S. Cl. .................. 536/23.1; 435/6; 435/69.1; 536/23.5; 536/24.1

(58) Field of Classification Search .................. 536/27, 536/22.1, 23.1, 24.1, 25.3, 24.3–24.33; 435/6, 435/810; 436/501; 935/77, 78
See application file for complete search history.

(56) References Cited

FOREIGN PATENT DOCUMENTS

| WO | 8905358 | 6/1989 |
|---|---|---|
| WO | 8908146 | 9/1989 |
| WO | 9008838 | 8/1990 |

OTHER PUBLICATIONS

Walder et al. Proc. Natl. Acad. Sci. 85: 5011-5015, 1988.*
van der Krol, et al., *BioTechniques*, 6:958-976 (1988).
Inoue, et al., *Nucleic Acids Symposium Series*, 18:221-224 (1987).
Markus-Sekura, et al., *Nucleic Acids Research*, 15:5749-5763 (1987).
Agrawal, et al., *Proc. Natl. Acad. Sci. (USA)*, 85:7079-7083 (1988).
Stein, et al., *Nucleic Acids Research*, 16:3209-3221
Sun, et al., *Biochemistry*, 27:6039-6045 (1988).
Sarin, et al., *Proc. Natl. Acad. Sci. (USA)*, 85:7448-7451 (1988).
Quartin, et al., *Biochemistry*, 28:1040-1047 (1989).
Maniatis, et al., *Molecular Cloning: A Laboratory Manual*, Cold Spring Harbor Laboratory, pp. 109-110 (1982).
Minshull, et al., *Nucleic Acids Research*, 14:6433-6451 (1986).
Cazenave, et al., *Nucleic Acids Research*, 15:4717-4736 (1987).
Miller, et al., *Biochimie*, 67:769-776 (1985).
Maher, et al., *Nucleic Acids Research*, 16:3341-3358 (1988).
Smith, et al., *Proc. Natl. Acad. Sci. (USA)* 83:2787-2791 (1986).
Agris, et al., *Biochemistry*, 25:6268-6275 (1986).
Melton, et al., *Nucleic Acids Research*, 12:7035-7056 (1984).
Agrawal, et al., *Tetrahedron Letters*, 28:3359-3542 (1987).
Dash, et al., *Proc. Natl. Acad. Sci. (USA)* 84:7896-7900 (1987).
Quartin, et al., *Nucleic Acids Research* 17:7253-7262 (1989).
Brakel et al, "Number and Distribution of Methylphosphonate Linkages in Oligodeoxynucleotides Affect Exo- and Endonuclease Sensitivity and Ability to Form RNase II Substrates", *Nucleic Acids Research* vol. 17, No. 18, pp. 7253-7262 (1989).

* cited by examiner

*Primary Examiner*—Shubo (Joe) Zhou
(74) *Attorney, Agent, or Firm*—Natalie Bogdanos, Esq.; Ronald C. Fedus, Esq.; Cheryl H. Agris

(57) ABSTRACT

Disclosed is a nuclease resistant nucleotide compound capable of hybridizing with a complementary RNA in a manner which inhibits the function thereof, which modified nucleotide compound includes at least one component selected from the group consisting of $MN_3M$, $B(N)_xM$ and $M(N)_xB$ wherein N is a phosphodiester-linked modified 2'-deoxynucleoside moiety; M is a moiety that confers endonuclease resistance on said component and that contains at least one modified or unmodified nucleic acid base; B is a moiety that confers exonuclease resistance to the terminus to which it is attached; and x is an integer of at least 2.

3 Claims, No Drawings

MODIFIED NUCLEOTIDE COMPOUNDS

This is a continuation of application Ser. No. 07/446,235 filed on Dec. 4, 1989 now abandoned.

BACKGROUND OF THE INVENTION

1. Field of the Invention

The present invention relates to the field of oligo- and polynucleotides, more particularly to modified oligo- and polynucleotides suitable for therapeutic and imaging purposes, including those which require the delivery of such oligo- and polynucleotides either into cells or to cell surfaces.

2. Brief Description of the Prior Art

Oligonucleotides and oligonucleotide analogs which are complementary to messenger RNAs encoded by human, animal, plant, microorganism and viral genomes have been shown to be effective for inhibiting or otherwise regulating gene expression, such as by hybrid arrest of translation. This has prompted several groups of workers to attempt to develop various types of therapeutic "antisense" oligo- and polynucleotides. For a recent review, see van der Krol, et al., *Modulation of Eucaryotic Gene Expression by Complementary RNA or DNA Sequences*, Biotechniques, 6:958-976 (1988).

One mechanism by which phosphodiester oligodeoxynucleotides have been found to promote hybrid arrest of translation is through RNase H cleavage of the RNA in an RNA:oligodeoxynucleotide duplex. See, Minshull and Hunt, *The Use of Single-Stranded DNA and RNase H to Promote Quantitative Hybrid Arrest of Translation of mRNA/DNA Hybrids in Reticulocyte Lysate Cell-Free Translations*, Nucleic Acids Research, 14:6433-6451 (1986); Cazenave, et al., *Enzymatic Amplification of Translation Inhibition of Rabbit Beta-Globin mRNA Mediated by Anti-Messenger Oligodeoxynucleotides Covalently Linked to Intercalating Agents*, Nucleic Acids Research, 15:4717-4736 (1987); and Dash, et al., *Selective Elimination of mRNAs In Vivo: Complementary Oligodeoxynucleotides Promote RNA Degradation by an RNase H-Like Activity*, Proc. Nat. Acad. Sci. USA, 84:7896-7900 (1987).

In view of this, sensitivity to RNase H is one of the properties that should be considered when developing effective therapeutic antisense oligonucleotides. Unmodified oligonucleotides with phosphodiester linkages can complex with RNA to form RNase H substrates but are not nuclease resistant. One method of achieving a high degree of efficiency of translation inhibition is to chemically alter the oligodeoxynucleotide in order to facilitate its entry into the cell and increase its half-life, while maintaining its affinity for the specific RNA of interest. Thus, other aspects of this undertaking would include the development of antisense oligonucleotides or polynucleotides with modifications that result in reduced sensitivity of these agents to nucleases which might diminish their effectiveness or render them inactive.

Inoue, et al., *Sequence-Dependent Hydrolysis of RNA using Modified Oligodeoxynucleotide Splints and RNase H*, Nucleic Acids Symposium Series, 18:221-224 (1987) describes a method of cleaving RNA in vitro in a site-specific manner using modified oligonucleotides and RNase H.

Partially or completely substituted phosphorothioates have also been tested for antisense function. See Marcus-Sekura, et al., *Comparative Inhibition of Chloramphenicol Acetyltransferase Gene Expression by Antisense Oligonucleotide Analogues having Alkyl Phosphotriester, Methylphosphonate and Phosphorothioate Linkages*, Nucleic Acids Research, 15:5749-5763 (1987) as well as Agrawal, et al., *Oligodeoxynucleotide Phosphoramidates and Phosphorothioates as Inhibitors of Human Immunodeficiency Virus*, Proc. Nat. Acad. Sci. USA, 85:7079-7083 (1988). They exhibit varying degrees of resistance to a variety of nucleases. Fully substituted phosphorothioate oligodeoxynucleotides form RNase H-sensitive hybrids, as reported in Stein, et al., *Physicochemical Properties of Phosphorothioate Oligodeoxynucleotides*, Nucleic Acids Research, 16:3209-3221 (1988).

By contrast, many oligonucleotides containing fully-substituted nuclease-resistant sugar-phosphate backbones are incapable of forming RNase H-sensitive hybrids with target DNAs. See, for example, Sun, et al., *Sequence-Targeted Cleavage of Nucleic Acids by Oligo-alpha-thymidylate-Phenanthroline Conjugates: Parallel and Antiparallel Double Helices are formed with DNA and RNA, Respectively*, Biochemistry, 27:6039-6045 (1988). Alpha-phosphodiesters form antiparallel helices with complementary RNA, but not with DNA. Nevertheless, although the alpha-linkages are nuclease-resistant, alpha DNA-RNA hybrids are not substrates for RNase H. Aminophosphonates or triesters can be formed by modifying the oxidation step in hydrogen-phosphonate synthesis. These uncharged linkages should interfere with the ability to form an RNase H-sensitive hybrid.

Oligodeoxynucleotide analogs containing methylphosphonate linkages have been shown to have an antisense effect in vitro. See, Miller, et al., *Control of Ribonucleic Acid Function by Oligonucleoside Methylphosphonates*, Biochimie, 67:769-776 (1985) as well as Maher and Dolnick, *Comparative Hybrid Arrest by Tandem Antisense Oligodeoxyribonucleotides or Oligodeoxyribonucleoside Methylphosphonates in a Cell-Free System*, Nucleic Acids Research, 16:3341-3358 (1988). An antisense effect has been shown in vivo. See, Sarin, et al., *Inhibition of Acquired Immunodeficiency Syndrome Virus by Oligodeoxynucleoside Methylphosphonates*, Proc. Nat. Acad. Sci. USA, 85:7448-7451 (1988); Smith, et al., *Antiviral Effect of an Oligodeoxynucleoside Methylphosphonate Complementary to the Splice Junction of Herpes Simplex Virus Type 1 Immediate Early Pre-mRNAs 4 and 5*, Proc. Nat. Acad. Sci. USA, 83:2787-2791 (1986); and Agris, et al., *Inhibition of Vesicular Stomatitis Virus Protein Synthesis and Infection by Sequence Specific Oligodeoxynucleoside Methylphosphonate*, Biochemistry, 25:6268-6275 (1986). Methylphosphonamidite nucleosides can be incorporated during phosphoramidite synthesis to yield partially substituted structures, as reported by Marcus-Sekuar, supra. Reducing the number of methylphosphonate linkages leads to greater hybrid stability, as reported by Quartin and Wetmur, *Effect of Ionic Strength on the Hybridization of Oligodeoxynucleotides with Reduced Charge Due to Methylphosphonate Linkages to Unmodified Oligodeoxynucleotides Containing the Complementary Sequence*, Biochemistry, 28:1040-1047 (1989).

In a cell-free translation system, it was determined that the action of RNase H was not involved in the antisense effect seen with fully methylphosphonate-substituted oligodeoxynucleotides, and that such compounds did not form RNase H-sensitive hybrids with complementary RNA. See, Maher and Dolnick, supra.

Oligodeoxynucleotides with modified ends have been shown to have relative resistance to exonucleases. For example, see Agrawal and Goodchild, *Oligodeoxynucleotide Methylphosphonates: Synthesis and Enzymic Degradation*, Tetrahedron letters, 28:3539-3542 (1987).

Notwithstanding the progress made and reported as described above, these efforts have not been entirely successful in permitting the rational design of stable, therapeutically-effective oligo- and polynucleotides such as has now become possible as a result of the present invention. Particularly, no one has examined the ability of mixed oligodeoxynucleotides to form RNase H-sensitive substrates as a factor in optimizing antisense function. In addition, heretofore, no one has correlated the ability to form RNase H sensitive substrates with nuclease resistance.

SUMMARY OF THE INVENTION

The present invention provides oligo- and polynucleotide analog constructs complementary to at least a portion of and effective to inhibit the function of an RNA of the organism to which it is administered or of a foreign organism or virus therein. The invention was made possible by examining the correlation between positioning of methylphosphonate or other substitutions in oligodeoxynucleotides and their sensitivity to exo- and endonucleases as well as their ability to form RNase H substrates.

In one aspect, the invention provides a compound having a sequence of 2 or more phosphodiester-linked nucleosides which are nuclease resistant therein. In another aspect, the invention provides a modified nuclease-resistant nucleotide compound which includes at least one component selected from the group consisting of $MN_3N$, $B(N)_xM$ and $M(N)_xB$ wherein N is a phosphodiester-linked modified or unmodified 2'-deoxynucleoside moiety; M is a moiety that confers endonuclease resistance on the nucleotide component and contains at least one modified or unmodified nucleic acid base; B is a moiety that confers exonuclease resistance to the terminus to which it is attached; and x is an integer of at least 2.

In another aspect, the invention provides a method of inhibiting the function of an RNA, which method comprises contacting, under conditions permissive of hybridization, the RNA with a complementary modified nucleotide compound which includes at least one component selected from the group consisting of $MN_3M$, $B(N)_xM$ and $M(N)_xB$ wherein N is a phosphodiester-linked modified or unmodified 2'-deoxynucleoside moiety; M is a moiety that confers endonuclease resistance on the nucleotide component and contains at least one modified or unmodified nucleic acid base; B is a moiety that confers exonuclease resistance to the terminus to which it is attached; and x is an integer of at least 2. The above-described preferred embodiments relate particularly to the method of use of this compound.

The invention also provides a method of identifying oligo- or polynucleotides having a combination of increased nuclease resistance and the ability to from an RNase H substrate when in complex with an RNA.

An additional aspect of the invention provides a nucleotide compound which can be introduced into a living organism and will not be degraded before it can act as an effective agent for therapeutic or diagnostic applications. This compound includes at least one component selected from the group consisting of $MN_3M$, $B(N)_xM$ and $M(N)_xB$ wherein N is a phosphodiester-linked modified or unmodified 2'-deoxynucleoside moiety; M is a moiety that confers endonuclease resistance on the nucleotide component and contains at least one modified or unmodified nucleic acid base; B is a moiety that confers exonuclease resistance to the terminus to which it is attached; and x is an integer of at least 2.

The compounds described in this invention are useful as "antisense" oligo- or polynucleotides for therapeutic or imaging applications and have combined improved properties of resistance to endo- and exonucleases, as well as the ability to form RNase H-sensitive hybrids. Particularly advantageous chemistries for the syntheses of these compounds are provided, as are methods for their use.

DETAILED DESCRIPTION OF PREFERRED EMBODIMENTS

As previously noted, the preset invention provides a composition of an oligonucleotide or polynucleotide compound having a sequence of 2 or more phosphodiester-linked nucleosides and which is nuclease resistant. The invention also provides a method for inhibiting the function of an RNA, including functions relating to expression, splicing and translation of the RNA. The compounds of the present invention have a number of valuable uses, including therapeutic uses in which the sequence is capable of inhibiting or preventing the expression of deleterious protein products or the replication or viability of pathogens. Thus, there is provided a method of treating an organism for infection by a foreign organism or virus by administering a therapeutically effective amount of the compound of the invention. The compound is administered by a route which brings it into contact with the cell, organism or virus upon which it is intended to impart its therapeutic effect.

As disclosed above, N is a phosphodiester-linked unmodified or modified 2'-deoxynucleoside moiety. Preferably, it is an unmodified 2'-deoxynucleoside moiety. When modified, exemplary modified forms include 2, 6-diaminopurine, uracil, inosine, 5-halogenated uracil or cytosine, substituted or unsubstituted 7-deazaguanine, 7-deazaadenine, 7-deasainosine, or a methylated adenine, thymine, cytosine or quanine.

M is a moiety that confers endonuclease resistance on the nucleotide component and contains at least one modified or unmodified nucleic acid base. Preferably, it is a $C_1$-$C_4$ alkylphosphonate, such as a methylphosphonate, or is an alpha-phosphodiester linkage. Other examples of M include those selected from the group consisting of an aminophosphonate, phosphotriester, phosphoramidate, carbamate or morpholino-substituted nucleotide. M can also confer exonuclease resistance.

B is a moiety that confers exonuclease resistance to the terminus to which it is attached, preferably directly or indirectly to the deoxyribose moiety of at least one of the 3'- and 5'-terminal nucleotides. Examples of B include an intercalating agent, a methylthiophosphate, a carbodiimide and an N-hydroxybenzotriazole. B can also be an isourea, a polypeptide or a protein. By way of an additional example, where the modified nucleotide has the formula $M(N)_xB$, B can be a modified or unmodified 2', 3'-dideoxyribose nucleotide.

As used herein, x is an integer of at least 2, preferably 2 or 3.

The term "nuclease resistant" refers to the decreased ability of a compound to serve as a substrate for endo- or exonucleases, such that the compound is either not degraded, or is degraded more slowly than unmodified phosphodiester-linked nucleosides when contacted with these enzymes.

A particularly preferred embodiment is a nuclease-resistant nucleotide compound which includes at least one sequence of the formula $MN_3M$ wherein N is an unmodified phosphodiester-linked nucleoside moiety selected from the group of adenine, guanine, thymine and cytosine and M is a 2'-deoxynucleoside methylphosphonate. In this embodiment, M confers endonuclease and exonuclease resistance, thereby additionally performing the function of B.

The invention also provides a method of inhibiting the function of an RNA, which method comprises contacting, under conditions permissive of hybridization, the RNA with a complementary modified nucleotide compound which includes at least one component selected from the group consisting of $MN_3M$, $B(N)_xM$ and $M(N)_xB$ wherein N is a phosphodiester-linked modified or unmodified 2'-deoxynucleoside moiety; M is a moiety that confers endonuclease resistance on the nucleotide component and contains at least one modified or unmodified nucleic acid base; B is a moiety that confers exonuclease resistance to the terminus to which it is attached; and x is an integer of at least 2. The above-described preferred embodiments relate particularly to this method of use of the compound.

The invention also provides a method of identifying oligo- or polynucleotides having a combination of nuclease resistance and the ability to form an RNase H substrate when in an RNA:oligo- or polynucleotide complex. This method comprises (i) preparing the modified oligo- or polynucleotide compounds; (ii) selecting by exo- and endonuclease digestion those oligo- or polynucleotides of (i) which are nuclease-resistant as shown by being capable of forming and electrophoretically migrating as a duplex with a complementary nucleotide compound; and (iii) selecting by RNase H digestion those of the nuclease-resistant nucleotide compounds of (ii) which act as substrates for RNase H when in complex with a complementary RNA.

The oligodeoxynucleotides used in the studies described below are presented in Table 1, where they are grouped into complementary sets designated as sense or antisense.

TABLE 1

| Oligodeoxynucleotides | | | |
|---|---|---|---|
| Sense | | Antisense | |
| Sequence | Name | Sequence | Name |
| GGATGCAGCTAAGTCAAG | 18-P-4 | CTTGACTTAGCTGCATCC | 18-P-3 |
| ATGCAGCTAAGTCA | 14-P-4 | TGACTTAGCTGCAT | 14-P-3 |
| AT<u>GC</u>AG<u>CT</u>AA<u>GT</u>CA | 14-G-4 | TG<u>A</u>CTT<u>A</u>GCTGC<u>AT</u> | 14-A-3 |
| A<u>T</u>GCAGC<u>T</u>AAG<u>T</u>CA | 14-T-4 | TGAC<u>T</u>TAGC<u>T</u>GCAT | 14-C-3 |
| ATG<u>C</u>AG<u>CT</u>AAGT<u>C</u>A | 14-C-4 | TGA<u>CT</u>TAG<u>CT</u>GCAT | 14-Me⁶a-3 |
| ATGCAGCTAAG<u>TC</u>A | 14-C/T-4 | TGA<u>CT</u>TAG<u>CT</u>GCAT | 14-Me⁶b-3 |
| | | TGA<u>CT</u>TAGC<u>T</u>GCAT | 14-Me⁵a-3 |
| | | TG<u>A</u>C<u>TT</u>AGCTGC<u>A</u>T | 14-Me⁵b-3 |
| CGCCATGCAGCCCCAGTC | 18-P-2 | TGGGGCTGCATG | 12-P-1 |
| | | TGGGG<u>CTGC</u>ATG | 12-Me⁴-1 |
| | | C<u>TGGGGCTGC</u>AT | 12-Me⁵a-1 |
| | | TGGG<u>GCTGC</u>ATG | 12-Me⁵-b-1 |
| | | TGGGG<u>CTGC</u>ATG | 12-Me⁵-1 |
| | | <u>TGGGGCTGCAT</u>G | 12-Me¹⁰-1 |

* Underlined bases are those with a 3' methylphosphonate linkage.

Marker phosphodiester oligodeoxynucleotides were 5'-labeled with ³²P using T4 polynucleotide kinase and purified using a spun column of Sephadex G-50 in water. See, Maniatis, et al., *Molecular Cloning*, Cold Spring Harbor Laboratory, New York (1982).

Gel Migration Analysis

All methylphosphonate-substituted oligodeoxynucleotides were quantitated by a previously described gel migration analysis procedure with their respective 5'-³²P labeled complementary phosphodiester oligodeoxynucleotides. See, Quartin and Wetmur, supra. Briefly, the assay procedure was as follows: Marker phosphodiester oligodeoxynucleotides were 5'-labeled with ³²P using T4 polynucleotide kinase and purified using a spun column (Maniatis, et al., 1982) of Sephadex G-50 in water. Annealing to nuclease-treated, complementary oligodeoxynucleotides was carried out at room temperature for 15 minutes prior to electrophoresis. Control annealing reactions were carried out in appropriate enzyme buffers. Samples were loaded onto a 20% acrylamide gel in 2.5% Ficoll 400. Gel electrophoresis was carried out at 4° C. at 400 volts, 5-15 milliamps in TBE (89 mM Tris-Cl, 89 mM borate, 1 mM EDTA) buffer for 2-4 hours. The gels were dried and examined by autoradiography.

Nuclease action by a given quantity of enzyme on substituted oligodeoxynucleotides was compared to results with equivalent quantities of control phosphodiester analogs.

Labeled 18-P-4, which serves as the marker oligodeoxynucleotide has a lower mobility when hybridized to any of its complementary sequences, such as 14-P-3 or 14-Me⁶a-3. When an enzyme-treated oligodeoxynucleotide fails to decrease the mobility of 18-P-4, it is no longer forming a duplex, indicating a sensitivity to the tested nuclease.

EXAMPLE 1

Assay for Nuclease Sensitivity

Oligonucleotide Preparation

Oligodeoxynucleotides were synthesized on an Applied Biosystems Model 380B DNA Synthesizer. Phosphodiester linkages were generated by standard phosphoramidite chemistry, and methylphosphonate bonds were introduced by the coupling of metylphosphonamidite monomers. Hydrolysis of the base-protecting groups and cleavage from the support for phosphodiester oligodeoxynucleotides was accomplished by NH₄OH treatment, which was followed by ethanol precipitation. Oligodeoxynucleotides containing mixed phosphodiester and methylphosphonate bonds were deprotected and released in ethylenediamine:ethanol (1:1) for 7 hours at room temperature. Alternatively, in addition to this treatment, the support material was treated in NH₄OH for 2 hours at room temperature. See, Sarin, et al., supra. These oligodeoxynucleotides were purified by 4 M ammonium acetate elution from NACS Prepac columns (Bethesda Research Laboratories, Bethesda, Md.).

EXAMPLE 2

DNase I and DNase II Endonuclease Sensitivity

Analysis of nuclease sensitivity is based on the ability of an oligodeoxynucleotide to form a duplex with and affect the migration through a gel of a ³²P-labeled complementary oligodeoxynucleotide. Nuclease action by a given quantity of enzyme on substituted oligodeoxynucleotides is compared to results with control phosphodiester analogs.

For DNase I and DNase II endonuclease sensitivity, this was determined by the gel shift assay, performed essentially as described in Quartin and Wetmur (1989), supra. Methylphosphonate-containing oligodeoxynucleotides with 1-5 adjacent phosphodiester linkages were tested as follows.

Nuclease digestions of oligodeoxynucleotides were carried out in 10 ul volumes under the conditions described below for each enzyme. Bovine pancrease DNase I (1 ug) (3.1.4.5) (Bethesda Research Laboratories, Bethesda, Md.) was used in a solution containing 50 mM sodium acetate (pH 6.5), 10 mM $MgCl_2$ and 2 mM $CaCl_2$ at 37°0 C. Bovine spleen DNase II (20 units) (3.1.4.6) (Bethesda Research Laboratories, supra) was used in a solution containing 0.8 mM $MgSO_4$ and 83.3 mM HOAc (pH 4.6) at 25° C. Enzyme quantities for digestion reactions were determined by titration with the phosphodiester oligodeoxynucleotide.

The DNase I reaction was stopped by the addition of EDTA to 25 mM and incubation at 70° C. for 10 minutes. The DNase II reaction was stopped by addition of EDTA to 21 mM and Tris-OH to pH 6.0, followed by incubation at 70° C. for 30 minutes. Both reaction solutions were brought to at least 100 mM NaCl for oligodeoxynucleotide annealing.

Table 2 presents the relative half-lives for digestion of oligodeoxynucleotides by the endonucleases DNase I and DNase II. The half-lives of the oligonucleotides with methylphosphonate linkages are presented relative to the control oligonucleotide, 14-P-3. The half-life for digestion of 14-P-3 by DNase I was on the order of 10 minutes. 14-A-3, which has an internal span of five phosphodiester linkages, is as sensitive to DNase I as the control 14-P-3. 14-$Me^6$a-3 has alternating diester and methylphosphonate linkages and was over 600 times more resistant to DNase I than 14-P-3. The general trend is that as the phosphodiester span is decreased, the oligodeoxynucleotide becomes more resistant to endonuclease activity. The DNase II reactions were much slower than those for DNase I (half-life for 14-P-3 digestion of 10 hours). Within the time-frame of the experiments, the relative half-lives for the most resistant methylphosphonates can only be designated as greater than 5.

TABLE 2

Endonuclease Digestion Susceptibility

| Oligomer | Endonuclease Relative Half-Life | |
|---|---|---|
| | DNase I | DNase II |
| 14-P-3 | 1 | 1 |
| 14-A-3 | 1 | >5 |
| 14-C-3 | 6 | 2 |
| 14-$Me^5$b-3 | 12 | >5 |
| 14-$Me^5$a-3 | 300 | >5 |
| 14-$Me^6$b-3 | >600 | >5 |
| 14-$Me^6$a-3 | >600 | >5 |

EXAMPLE 3

Exonuclease (5'- and 3'-) Sensitivity

Nuclease resistance of the oligodeoxynucleotides was detected following digestion with 5'- and 3'-exonucleases by the ability to cause a change in the electrophoretic mobility ("gel-shift") of a complementary phosphodiester-linked oligodeoxynucleotide.

Nuclease digestions of oligodeoxynucleotides were carried out in 10 ul volumes under the conditions described below for each enzyme. Bovine spleen phosphodiesterase (3.1.4.18) (Sigma, St. Louis, Mo.) was used in a solution containing 0.1 M sodium citrate (pH 6.0) and 5 mM EDTA at 37° C. Snake venom phosphodiesterase from *Crotalus adamanteus* (3.1.4.1) (Sigma, supra) was used in a solution containing 0.2 M Tris-Cl (pH 9.0) at 37° C. Enzyme quantities for digestion reactions were determined by titration with the phosphodiester oligodeoxynucleotide.

The snake venom phosphodiesterase reaction was stopped by the addition of EDTA to 25 mM and incubation at 70° C. for 10 minutes. The spleen phosphodiesterase reaction was stopped by incubation at 70° C. for 10 minutes. Both reaction solutions were brought to at least 100 mM NaCl prior to oligodeoxynucleotide annealing.

The results of the spleen and snake venom exonuclease studies are summarized in Table 3. The half-life of each oligonucleotide is presented relative to that of its respective control, unmodified oligonucleotide sequences, 14-P-3 or 14-P-4.

The half-time for spleen exonuclease digestion of the control oligodeoxynucleotides was about 30 minutes for the enzyme concentration used. All of the partially modified oligodeoxynucleotides tested with spleen exonuclease were more than 200 times as resistant as their respective controls based on the absence of detectable cleavage following overnight digestion with appropriately increased enzyme concentrations. The oligodeoxynucleotides 14-C-4, 14-G-4 and 14-T-4 were apparently shortened, as evidenced by a slight increase in the electrophoretic mobility of the hybrid. The half-time for venom exonuclease digestion of the control oligodeoxynucleotides was about 12 minutes for the enzyme (Sigma) concentration used. The modified oligodeoxynucleotide with the shortest relative half-life (14-G-4) had its first methylphosphonate bond as the third linkage in from the 3'-end, while the other oligodeoxynucleotides tested had a methylphosphonate as the first or second linkage from the 3'-end. In another study, using Worthington venom exonuclease, the presence of two consecutive methylphosphonate linkages at the 3'-end (14-C/T-4) yielded approximately a two-fold increase in the half-life of the oligodeoxynucleotide, as compared to 14-C-4, which has only one methylphosphonate linkage at the 3'-end.

TABLE 3

Exonuclease Digestion Susceptibility

| Oligomer | Exonuclease Relative Half-Life | |
|---|---|---|
| | Spleen (5'->3'-) | Venom (3'->5'-) |
| *14-P-3 | 1 | 1 |
| *14-P-4 | 1 | 1 |
| 14-C-3 | >>200 | >500 |
| 14-G-4 | >>200 | 100 |
| 14-A-3 | >>200 | >>500 |
| 14-T-4 | >>200 | >500 |
| 14-$Me^6$a-3 | >>200 | >>500 |

*Indicates control oligonucleotides

The above data demonstrate that single nuclease-resistant internucleotide linkages near the termini serve to greatly enhance the resistance of oligodeoxynucleotides to exonucleolytic enzymes.

EXAMPLE 4

RNase H Substrate Activity

The ability to act as an RNase H substrate, i.e., to direct RNase H cleavage of complementary RNA, was tested using the plasmid pSP65-ALA-D as follows.

The plasmid pSP65-ALA-D is a derivative of the SP 6 cloning vector pSP65 described in Melton, et al., *Efficient in Vitro Synthesis of Biologically Active RNA and RNA Hybridization Probes from Plasmids Containing a Bacteriophage SP6 Promoter*, Nucleic Acids Research, 12:7035-7056 (1984). It contains the cDNA sequence of delta-aminolevulinic acid dehydratase (ALA-D), a heme biosynthetic enzyme, inserted in the sense orientation in the Pst I site of the polylinker. Regarding ALA-D, see Wetmur, et al., *Human Alpha-Aminolevulinate Hydratase: Nucleotide sequence of a Full-length cDNA Clone*, Proc. Nat. Acad. Sci. USA, 83:7703-7707 (1986). A partial structure is generally as follows:

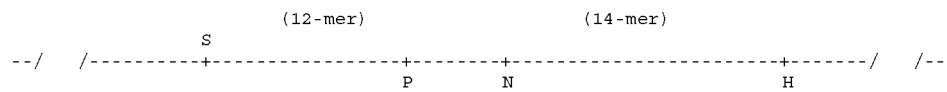

wherein the 12-mer and 14-mer labels are centered over oligodeoxynucleotide binding sites and the restriction endonuclease sites for runoff transcription are: P=PvuII, N=NcoI, H=HindIII and S=start of transcription.

Plasmid pSP65-ALA-D (1 ug) was digested with one of HindIII, NcoI, or PvuII and then extracted with phenol, extracted with chloroform:isoamyl alcohol (24:1), and ethanol precipitated. The pellet was washed with 70% ethanol, dried, and resuspended in water (200 ng/ul). The in vitro transcription reaction contained approximately 200 ng of linearized pSP65-ALA-D, all four ribonucleoside triphosphates (0.4 mM, cold), 20 uCi alpha-$^{32}$P-CTP (specific activity 800 Ci/mmol), 1 mM DTT, 40 mM Tris-HCl (pH 7.9), 6 mM MgCl$_2$, 2 mM spermidine-[HCl] and 15 units of SP6 RNA polymerase, and was incubated for one hour at 37° C. Samples were extracted, precipitated and dried, and then resuspended in water (10-20 ul).

Resuspended transcript (1 ul) was annealed with antisense oligodeoxynucleotide (20 ng), in 20 mM Tris-HCl (pH 7.5), 10 mM MgCl$_2$, 100 mM KCl, 10 mM DTT, and 5% (w/v) sucrose, in the presence of 10 units of the inhibitor RNase (9 ul total volume) (Promega Corp., Madison, Wis.). Following one minute incubation at 60° C., annealing mixtures were incubated at room temperature (22° C.) for 30 minutes. Then, *E. coli* RNase H (1 ul; 2 units; 3.1.26.4; BRL) was added and the reactions were incubated for 60 minutes at 37° C. EDTA (1 ul; 0.1 M) was added to stop the reaction. Samples were extracted, ethanol precipitated, dried and resuspended in RNA loading buffer (10 ul; 67% formamide and 20% formaldehyde). Following incubation at 60° C. for 5 minutes, samples were run on 6% denaturing (8 M urea) acrylamide gels at 350 volts, 45 mAmps, for 1 hour at room temperature. Results were visualized by autoradiography.

Partially Modified Oligodeoxynucleotides in RNase H Substrates $^{32}$P-labeled runoff transcripts were made from pSP6-ALA-D and incubated with various oligodeoxynucleotides in the presence of RNase H. The control phosphodiester oligodeoxynucleotide, 14-P-3, and the methylphosphonate-substituted oligodeoxynucleotides, 14-A-3, and 14-C-3 formed RNase H substrates, while 14-Me$^6$a-3 did not, even up to a concentration of 10 ug/ml. In addition, 14-Me$^5$a-3 and 14-Me$^5$b-3 were able to form RNase H substrates. However, the 14-mer binding site appeared to be a poor site for RNase H digestion since full cleavage of the RNA was never observed, perhaps due to secondary structure in the RNA at this region.

A set of 12-mer oligodeoxynucleotides, including the control phosphodiester oligodeoxynucleotide, 12-P-1, was tested. Using the NcoI runoff transcript, which is completely cleaved by RNase H in the presence of 12-P-1, it was observed that 12-Me$^4$-1 and 12-Me$^5$a -1 permitted cleavage of most of the RNA, while 12-Me$^5$b-1, 12-Me$^5$-1 and 12-Me$^{10}$-1 did not form RNase H substrates.

EXAMPLE 5

Stability of Oligonucleotides in Tissue Culture

Suspension cultures of B95-8 cells, an Epstein Barr virus-positive lymphoid cell line, were maintained in RPMI 1640 containing 10% heat inactivated fetal calf serum (FCS) and penicillin and streptomycin (all from Gibco) at 37° C. in a humidified 5% CO$_2$ incubator. Cells were maintained at concentrations at 4×10$^5$ to 2×10$^6$/ml.

For the stability studies, 200 ul of RPMI 1640 (only), 200 ul of complete medium and 200 ul of cell suspension were transferred to separate wells of 96 well tissue culture plates. Oligonucleotide were added to the wells at a final concentration of about 0.2 uM and were allowed to incubate for various times at 37° C. Samples (25 ul) were removed and incubated at 70° C. for 5-10 minutes to curtail further degradation and were then stored at −20° C. prior to gel migration analysis. The results of stability testing in cell suspensions are shown in Table 4.

TABLE 4

Tissue Culture Stabilities

| | | Relative Half-Life | |
|---|---|---|---|
| Culture condition | RPMI | +FCS | +FCS. B95-8 |
| 14-P-3 | Stable | 1 | 1 |
| 14-Me$^5$b-3 | Stable | 30 | 30 |
| 14-Me$^5$a-3 | Stable | 30 | 30 |

TABLE 4-continued

Tissue Culture Stabilities

| | | Relative Half-Life | |
|---|---|---|---|
| Culture condition | RPMI | +FCS | +FCS. B95-8 |
| 14-Me$^6$b-3 | Stable | 30 | 30 |
| 14-Me$^6$a-3 | Stable | 30 | 30 |

All of the oligonucleotides tested were stable to incubation in serum-free medium following incubation of up to 24 hours at 37° C. The stability of the individual oligonucleotides was altered by the presence of serum as degradation was similar in both complete medium and cell suspensions.

These results demonstrated that phosphodiester oligonucleotides have a half-life of less than 60 minutes in cell suspension (or complete medium). Results from similar experiments in serum-supplemented or conditioned medium using shorter time increments suggested a half-life of approximately 15 minutes. The oligodeoxynucleotides with methylphosphonate substitutions were significantly more stable than their phosphodiester analogs and displayed relatively similar half-lives of approximately 7.5 hours, independent of the arrangement of the methylphosphonate linkages. A 3'-exonucleolytic activity was evidenced by single stepwise cleavage of methylphosphonate-substituted oligodeoxynucleotides, 14-Me$^6$a-2 and 14 Me$^5$a-2, each of which contains a 3'-terminal-phosphodiester-linked thymidine residue and by the absence of cleavage of oligodeoxynucleotides 14-Me$^6$b-2 and 14-Me$^5$b-2, each of which contains a 3'-terminal-methylphosphonate-linked thymidine residue.

What is claimed is:

1. A modified nucleotide compound which contains at least one sequence having the formula MN$_3$M wherein N is a phosphodiester-linked unmodified 2'-deoxynucleoside moiety containing at least one guanine, adenine, cytosine or thymine moiety and M is a methylphosphonate-containing deoxynucleotide.

2. A method of inhibiting the function of an RNA, which comprises: contacting said RNA, under conditions permissive of hybridization, with a modified nucleotide compound which includes at least one sequence having the formula MN$_3$M wherein N is a phosphodiester-linked unmodified 2'-deoxynucleoside moiety containing at least one guanine, adenine, cytosine or thymine moiety and M is a methylphosphonate-containing deoxynucleoside.

3. A method of identifying a nucleotide compound having a combination of nuclease resistance and the ability to form an RNase H substrate when in complex with an RNA, which method comprises:
   (i) preparing modified nucleotide compounds;
   (ii) selecting by exo-and endonuclease digestion those modified nucleotide compounds of (i) which are nuclease-resistant as shown by being capable of forming and electrophoretically migrating as a duplex with a complementary nucleotide compound; and
   (iii) selecting by RNase H digestion those of the nuclease-resistance nucleotide compounds of (ii) which act as substrates for RNase H when hybridized with a complementary RNA.

* * * * *